(12) United States Patent
Puskas et al.

(10) Patent No.: US 8,232,299 B2
(45) Date of Patent: Jul. 31, 2012

(54) PHTHALIMIDE DERIVATIVES THAT INFLUENCE CELLULAR VESICULAR SYSTEMS, PHARMACEUTICAL COMPOSITIONS, AND USE THEREOF

(75) Inventors: Laszlo Puskas, Szeged (HU); Liliana Feher, Szeged (HU); Eszter Molnar, Pecs (HU)

(73) Assignee: Avidin Kft., Szeged (HU)

( * ) Notice: Subject to any disclaimer, the term of this patent is extended or adjusted under 35 U.S.C. 154(b) by 0 days.

(21) Appl. No.: 12/452,206

(22) PCT Filed: Jun. 20, 2008

(86) PCT No.: PCT/HU2008/000075
§ 371 (c)(1),
(2), (4) Date: Mar. 19, 2010

(87) PCT Pub. No.: WO2008/155594
PCT Pub. Date: Dec. 24, 2008

(65) Prior Publication Data
US 2010/0184762 A1 Jul. 22, 2010

(30) Foreign Application Priority Data
Jun. 21, 2007 (HU) ..................... 0700433

(51) Int. Cl.
A61K 31/4035 (2006.01)
A61K 31/4439 (2006.01)
A61K 31/5377 (2006.01)
C07D 413/12 (2006.01)
C07D 407/12 (2006.01)
C07D 209/48 (2006.01)

(52) U.S. Cl. ............... 514/339; 514/235.2; 514/417; 544/144; 546/277.1; 548/476

(58) Field of Classification Search .......... 514/339, 514/235.2, 417; 544/144; 546/277.1; 548/476
See application file for complete search history.

(56) References Cited

PUBLICATIONS

Niwayama et al. J. Med. Chem. 1996, 39, 3044-3045.*

(Continued)

Primary Examiner — Joseph Kosack
Assistant Examiner — Matthew Coughlin
(74) Attorney, Agent, or Firm — Olson & Cepuritis, Ltd.

(57) ABSTRACT

The present invention relates to compounds that are suitable for treatment of disease states and influence cellular vesicular systems, especially the formation and/or function of lipid droplets, said compound having the general formula I (I) wherein X are each independently hydrogen, halogen, —$C_{1-20}$-alkyl, —$C_{2-20}$-alkenyl, —$C_{2-20}$-alkinyl, —$C_{5-6}$-cykloalkyl, aryl, aralkyl, adamantyl, heterocyclic, hydroxyl, hydroxyalkyl, Or —N—($R^1$, $R^2$) group; n is 0, 1, 2, 3, or 4; $R^1$ and $R^2$ may each be independently hydrogen, straight or branching alkyl, cyclo-alkyl, aryl, aralkyl, heterocyclic group, wherein each is un-substituted or halogen substituted; or $R^1$ and $R^2$ together with the nitrogen in between them form a 5 or 6 member ring; A is a single bond, —O—, —S—, —CH2-, or —NH—; Y is O or S; Z is O or S; R' and R" are each independently methyl, ethyl, isopropyl, isobuthyl, sec-butyl or terc-butyl; with the restriction that: X(n) cannot all be fluorine, and A be a single bond, and Y, as well as Z be O, and R', as well as R" be isopropyl, and $R^1$ and $R^2$ be hydrogen at the same time. The present invention further relates to pharmaceutical compositions comprising such compounds and to use of such compounds for treatment of disease states.

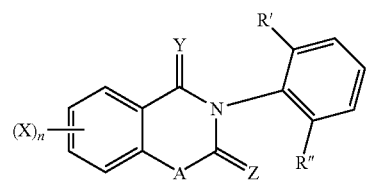

16 Claims, 7 Drawing Sheets

PUBLICATIONS

Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Cancer Drug Design and Discovery Neidle, Stephen, ed. (Elsevier/Academic Press, 2008) p. 427.*
Kamb, Nature Reviews Drug Discovery 4, 161-165 (Feb. 2005).*
Luo et al. Cell 2009, 136, 823-837.*

Bozza et al. Prostaglandins, Leukotrienes and Essential Fatty Acids, 2010, 82, 243-250.*

* cited by examiner

PHTHALIMIDE DERIVATIVES THAT INFLUENCE CELLULAR VESICULAR SYSTEMS, PHARMACEUTICAL COMPOSITIONS, AND USE THEREOF

This application is the National Stage of PCT/HU2008/000075, filed on Jun. 20, 2008, which is incorporated herein by reference in its entirety.

The present invention relates to compounds that are suitable for treatment of disease states and influence cellular vesicular systems, especially the formation and/or function of lipid droplets, in addition, the present invention also relates to pharmaceutical compositions containing such compounds, as well as to their use for treatment of disease states associated with formation and/or function of lipid droplets, such as cancer, inflammation and treatment of different bacterial and viral infections.

One of the emerging research fields of recent years is investigation of lipid droplets or lipid bodies (both expressions can be found in the literature) as cellular organelles. Lipid droplets in cells are primarily responsible for lipid storage and transport. Their morphology and protein content can vary extensively (Denis J. Murphy et al.: *Mechanism of lipid-body formation*, TIBS 24, 1999 Mar., p. 109-115.), however, their formation in plants, animals and microorganisms is similar in several aspects. Deficiency in the function of lipid droplets in human cells can be linked to several diseases, such as fatty liver, obesity, atherosclerosis, type-2 diabetes, inflammatory diseases and cancer. The size of the lipid droplets is usually between 0.1 and 50 µm.

Influencing the formation and/or the function of the lipid droplets might positively influence those disease states where lipid droplets have any function.

Small molecules inhibiting the formation and/or movement of lipid droplets have potential anti-cancer effect, since the elevation of the intracellular fatty acid concentration—being in relation with the function of lipid droplets—can result in apoptosis as explained below. De novo fatty acid synthesis is characteristic of cancer cells. Ability of the cells other than fat cells for storing triglycerides made from saturated fatty acids is limited. Besides storage, cells can eliminate the accumulated fatty acids by oxidation (beta-oxidation). However, under hypoxic conditions, being characteristic of cancer cells, beta-oxidation is limited, and so, part of the accumulating fatty acids appear in the form of lipid droplets. Those fatty acids which are released, and which are not encapsulated into lipid vesicles will be incorporated into the endoplasmic reticulum membrane leading to its increased saturation, which will eventually destroy the structure and integrity of the endoplasmic reticulum membrane. As a consequence, calcium ions are released from the endoplasmic reticulum inducing apoptosis via mitochondria (Borradaile N M, Han X, Harp J D, Gale S E, Ory D S, Schaffer J E: *Disruption of endoplasmic reticulum structure and integrity in lipotoxic cell death. J. Lipid Res.* 2006 December; 47(12):2726-2737). Consequently, the inhibition of lipid droplet formation in tumor cells could lead to the destruction of such cells.

The number of lipid droplets is significantly increased during inflammation (Weller P F és Dvorak A M: *Arachidonic incorporation by cytoplasmic lipid bodies of human eosinophils. Blood* 65, 1985, 1269-1274; Weller P F és Dvorak A M: *Lipid bodies: intracellular sites for eicosanoid formation. Int. Arch. Allergy Immunol.* 105, 1994, 245-250). It was shown that lipid droplets have a key role in the metabolism of eicosanoids, and lipid droplets are the stores for phospholipids containing arachidonic acid, as well as for enzymes such as cyclooxygenase (prostaglandin and endoperoxydase synthase) and 5-lipoxygenase (Weller P. F. et al: Cytoplasmic lipid bodies of human neutrophilic leukocytes. Am. J. Pathol. 1989, 113, p. 947-959.), which are essential for the synthesis of prostaglandins, tromboxanes and leukotrienes.

Prostanoids, including prostaglandin (PG) D2, PGE2, PGF2a, PGI2 and thromboxane A2, regulate several physiologic functions and modulate inflammatory diseases such as rheumatoid arthritis, asthma, Crohn's disease and atherosclerosis (Ristimaki A.: *Cyclooxygenase 2: from inflammation to carcinogenesis. Novartis Found Symp.* 2004; 256:215-221).

Prostaglandins generated by cyclooxygenase-2 help tumor development by stimulating proliferation and angiogenesis, and inhibit programmed cell death and immune response (Marks F, Furstenberger G, Muller-Decker K.: Tumor promotion as a target of cancer prevention. Recent Results Cancer Res. 2007; 174:37-47).

It was shown by immunogold staining that in Crohn's disease of the colon a pro-inflammatory cytokine, TNF-alpha, in an intracellular location binds mainly to lipid droplets in fibroblasts, in eosinophil and neutrophil granulocytes, in macrophages, in phagocytes and in the epithelial absorption cells of the colon (Waltraud J. Beil et al.: Ultrastructural immunogold localization of subcellular sites of TNF-a in colonic Crohn's disease. J. Leukocyte Biology 58, 1995, 284-298.), that is why it is supposed that lipid droplets can have an important role in the development of Crohn's disease.

Development of atherosclerosis might also be related to formation of lipid droplets (Toda T, Leszczynski D E, Kummerow F A: *Morphological evidence of endogenous lipid production in swine ductus vasculature., Atherosclerosis.* 1980 October; 37(2):325-330).

Lipid droplets also have important role in the life cycle of several bacteria, such as the mycobacteria, which cause tuberculosis (Garton J N et al.: *Intracellular lipophilic inclusions of mycobacteria in vitro and in sputum, Microbiology* (2002), 148, 2951-2958).

The effect of Herpes simplex and influenza viruses on lipid metabolism has been investigated (Ambroseva T V, Votiakov V I, Andreeva O T, Serebriakova E V, Vladyko G V, Samarina M P: *Biull Eksp Biol Med.* 1992 September; 114(9):302-304). It was found that in acute herpes infection of rabbits a typical dyslipidemia occurs with increase of total cholesterol, beta-cholesterol and triglyceride levels. Study on herpes infection of human aortic cell cultures was also published where intracellular accumulation of free lipids was detected.

It can be seen from the above examples that lipid droplets play a role in the development of several disease states, and for that, the influence of formation and/or function of lipid droplets might have a favorable effect on such diseases.

The objective of the invention is to provide compounds that influence the formation and/or function of lipid droplets in a way that favorably influences certain disease states.

The inventors identified compounds that are believed to be novel over the prior art. Therefore, the present invention relates to compounds having the general formula I wherein n is 4;

X is three times halogen and the forth substituent represents heterocyclic or —N—($R^1$, $R^2$) group, wherein $R^1$ and $R^2$ may each represent independently hydrogen, straight or branched alkyl group, cycloalkyl group, aryl, aralkyl, heterocyclic group, wherein each is un-substituted or halogen substituted or methyl-pyridine group, ethylamino group, morpholino-propyl group; or R¹ and R² together with the nitrogen in between them form a 5 or 6 member ring;

A is a single bond, —O—, —S— or —NH—;

Y is O or S;

Z is O or S;

R' and R" are independently isopropyl group.

We realized our goals with compounds having the general formula I. Hence, the present invention relates to compounds suitable for treatment of disease states and for influencing cellular vesicular systems, especially the formation and/or function of lipid droplets, said compounds having the general formula I

I wherein n is 4;

X is three times halogen and the forth substituent represents heterocyclic or —N—(R¹,R²) group, wherein R¹ and R² may each represent independently hydrogen, straight or branched alkyl group, cycloalkyl group, aryl, aralkyl, heterocyclic group, wherein each is un-substituted or halogen substituted or methyl-pyridine group, ethylamino group, morpholino-propyl group; or R¹ and R² together with the nitrogen in between them form a 5 or 6 member ring;

A is a single bond, —O—, —S— or —NH—;

Y is O or S;

Z is O or S;

R' and R" are independently isopropyl group.

In a preferred embodiment of the invention A is a single bond.

In another preferred embodiment of the invention at least one of Y and Z is O or both are O.

In another preferred embodiment of the present invention R¹ is hydrogen.

In a preferred embodiment of the invention wherein X represents a halogen atom, the halogen is fluorine.

In another preferred embodiment R¹ and/or R² are/is un-substituted or halogen substituted ethyl, ethyl or trifluoro-ethyl group.

In another preferred embodiment R¹ and/or R² are/is eth-ylene-amine group.

In another preferred embodiment both of R' and R" are isopropyl group.

In another preferred embodiment the compound binding to the lipid droplet is selected from:

2-(2,6-diisopropylphenyl)-4-(ethylamino)-5,6,7-trifluor-oisoindoline-1,3-dione;

2-(2,6-diisopropylphenyl)-5-(ethylamino)-4,6,7-trifluor-oisoindoline-1,3-dione;

2-(2,6-diisopropylphenyl)-4-(2-amino-ethylamino)-5,6,7-trifluoroisoindoline-1,3-dione;

2-(2,6-diisopropylphenyl)-5-(2-amino-ethylamino)-4,6,7-trifluoroisoindoline-1,3-dione;

2-(2,6-diisopropylphenyl)-4,5,6-trifluoro-7-(2,2,2-trifluoro-ethylamino)isoindoline-1,3-dione;

2-(2,6-diisopropylphenyl)-4,5,7-trifluoro-6-(2,2,2-trifluoro-ethylamino)isoindoline-1,3-dione;

2-(2,6-diisopropylphenyl)-4-(pyridine-3-ylmethy)-amino)-5,6,7-trifluoroisoindoline-1,3-dione;

2-(2,6-diisopropylphenyl)-5-(pyridine-3-ylmethy)-amino)-4,6,7-(trifluoroisoindoline-1,3-dione;

2-(2,6-diisopropylphenyl)-4-(3-morpholine-4-yl-propy-lamino)-5,6,7-trifluoroisoindoline-1,3-dione;

2-(2,6-diisopropylphenyl)-5-(3-morpholine-4-yl-propy-lamino)-5,6,7-trifluoroisoindoline-1,3-dione;

2-(2,6-diisopropylphenyl)-4-(morpholino)-5,6,7-trifluor-oisoindoline-1,3-dione;

2-(2,6-diisopropylphenyl)-4-(1-cyclopentylamino)-5,6,7-trifluoroisoindoline-1,3-dione;

2-(2,6-diisopropylphenyl)-5-(1-cyclopentylamino)-4,6,7-trifluoroisoindoline-1,3-dione;

In another preferred embodiment of the present invention disease states are selected from the following group comprising: cancer, inflammation, Crohn's disease, atherosclerosis, bacterial or viral infections.

In a further preferred embodiment of the present invention the disease state is cancer.

In a further preferred embodiment of the present invention the disease state is inflammation.

In a further preferred embodiment of the present invention the disease state is bacterial or viral infection.

The present invention relates to pharmaceutical compositions that are suitable for treatment of disease states by influencing the formation and/or function of lipid droplets, those pharmaceutical compositions having one or more carriers and containing a compound according to the general formula I.

The pharmaceutical composition can be administered to the patients by oral, parental or any other known administration ways, as an example by implanted delivery devices. Route of administration can be defined according to disease state, gender, age and other factors influencing the course of the disease and the recovery. It is apparent for those skilled in the art that the physician can define other ways of administration based on all circumstances and information available.

Pharmaceutical composition according to the present invention can be used for treatment of humans, animals, especially mammals and in certain cases birds (for example viral or bacterial infections).

Pharmaceutical composition according to the present invention can be used also in combination treatments with other drugs, compounds or treatments suitable for treatment of the given disease state. For example pharmaceutical composition according to the present invention can be used together with radiotherapy and/or chemotherapy.

Pharmaceutical composition according to the present invention can also be used for prevention of the disease regarding humans or animals being prone to that disease for example due to predisposition or to hazard of infection.

Compounds of the present invention can also be used for prevention of the infection/disease at locations where cells, cell lines, viruses which cause diseases according to the present invention can occur, e.g. in health care institutes, research laboratories, diagnostic laboratories, etc.

The present invention further relates to use of compounds and pharmaceutical compositions according to formula I in treatments of disease states mentioned above.

The term "halogen" in the present context denotes a substituent selected from fluorine, chlorine, bromine, or iodine.

The term "aryl group" in the present context, alone or in combination with any other substituents, denotes one carbocyclic aromatic group or an aromatic ring system with more carbocyclic aromatic system. E.g. the term aryl includes phenyl or naphthyl ring systems.

The term "—$C_{1-20}$-alkyl" in the present context, alone or in combination with any other substituents, denotes for a straight chained or branched acyclic hydrocarbon with 1 to 20 carbon atoms. "—$C_{1-20}$-alkyl" group can include e.g. methyl, ethyl, propyl, butyl, hexyl, 1-methyl-ethyl, 1-methyl-propyl, 2-methyl-propyl, or 1,1-dimethyl-ethyl groups.

A "—$C_{2-20}$-alkenyl" term in the present context alone or in combination with any other substituents, denotes a straight chained or branched acyclic alkenyl substitutent, which has from 2 to 20 carbon atoms, and contains at least one double bond, like vinyl or allyl groups.

A "—$C_{2-20}$-alkinyl" term in the present context alone or in combination with any other substituents, denotes a straight chained or branched acyclic alkenyl substitutent, which has from 2 to 20 carbon atoms, and contains at least one triple bond.

A "—$C_{5-6}$-cycloalkyl" in the present context, alone or in combination with any other substituents, means a cycloalkyl substituent, containing 5 or 6 carbon atoms and includes for example cyclopentyl or cyclohexyl groups.

An "aralkyl" means an aryl substituted alkyl or cycloalkyl group.

Heterocyclyl group designates in the present context unsubstituted or halogen substituted alycyclic or aromatic ring that contains one nitrogen atom or methyl-pyridine group or morpholino-propyl group.

Hydroxyalkyl group means an alkyl group substituted by hydroxyl group.

Accordingly, the present invention discloses compounds that have favorable effects on disease states by binding to and influencing the formation and/or function of lipid droplets.

It should be noted that 2-(2,6-diizopropylphenyl)-4,5,6,7-tetrafluorisoindolin-1,3-dione (compound 2) presented in Japanese patent application JP10072346 also has the general formula I. It was shown that this compound inhibits the production of tumor necrosis factor. The same compound (compound 2) has anti-inflammatory effect too, according to Japanese patent JP10072346.

The following Examples serve to illustrate the invention and are not intended to limit the scope of protection.

EXAMPLE 1

2-(2,6-diisopropylphenyl)-4-(ethylamino)-5,6,7-trifluoroisoindole-1,3-dione (3a) and 2-(2,6-diisopropylphenyl)-5-(ethylamino)-4,6,7-trifluoroisoindole-1,3-dione (3b)

19 g (50 mmol) of 2-(2,6-diisopropylphenyl)-4,5,6,7-tetrafluoroisoindole-1,3-dione (2) was dissolved in 30 ml of chloroform (30 ml, a.r., Molar) and then ethylamine was added (2 ml, 70% v/v in water, Aldrich) thereto. The mixture was stirred at room temperature for 4 hours and cyclohexane (20 ml, Molar) was added, subsequently the solution was applied to silica gel column, which was equilibrated with chloroform-cyclohexane 1:3 v/v. The column was washed with chloroform-cyclohexane 1:3 v/v, and was subsequently eluted with chloroform-cyclohexane 1:1 v/v solution. The first fractionated product 3a was evaporated (yield: 6.9 g, 30.1%) and the purity of the product was checked by Thin Layer Chromatography (Rf: 0.39 (chloroform:cyclohexane 1:1 v/v)) and the mass of the product was confirmed by Mass Spectrometry (MW+1: 404.3). The second fractionated product 3b was evaporated (yield: 5.8 g, 28.7%) and the purity of the product was checked by Thin Layer Chromatography (Rf: 0.19 (chloroform:cyclohexane 1:1 v/v)) and the mass of the product was confirmed by Mass Spectrometry (MW+1: 404.2).

Figure 1A:
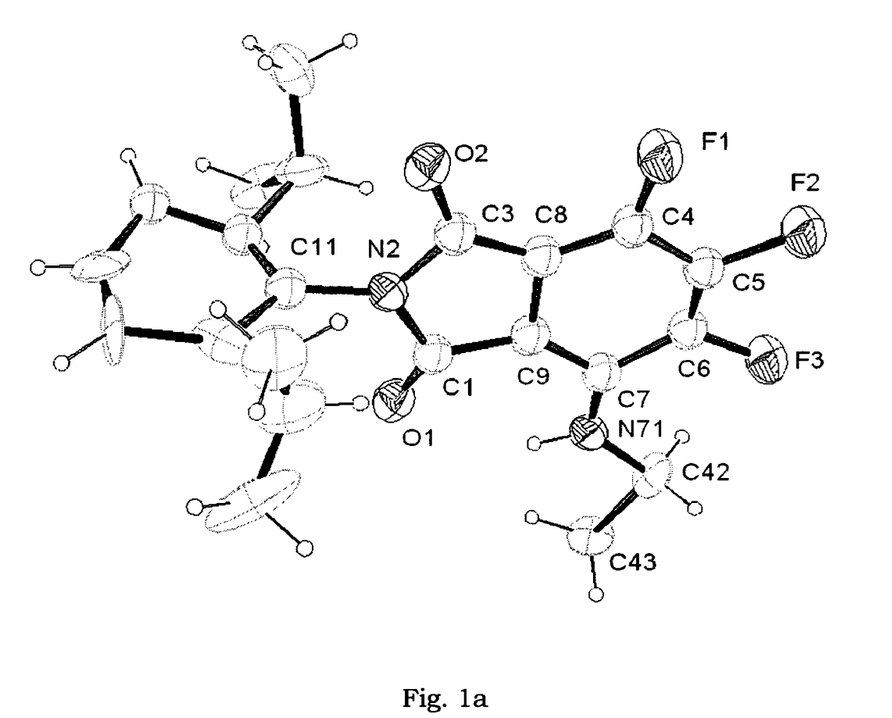
FIG. 1a shows crystal structure of a compound of the present invention, compound (3a), determined by X-ray diffraction, where hydrogen atoms as well as numbering of heavy atoms are also presented.
Figure 1B:
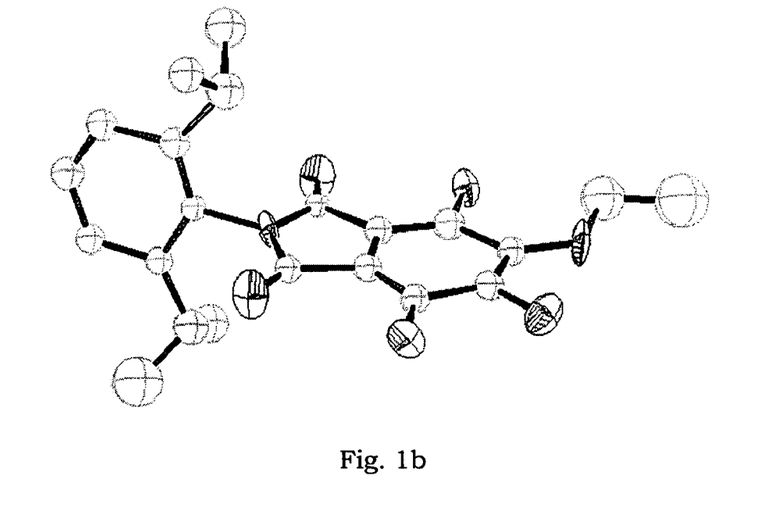
FIG. 1b shows crystal structure of another compound of the present invention, compound (3b), determined by X-ray diffraction, where hydrogen atoms as well as numbering of heavy atoms are not presented.

Crystal structure of compounds 3a and 3b was confirmed by one-crystal X-ray diffraction, and the resulted molecular structures can be seen in FIG. 1a (3a) and in FIG. 1b (3b). In the figures individual atoms were represented by elliptic rings with sizes proportional to the atomic displacement parameters in the three dimensional space (i.e. the bigger the elliptic ring, the more dynamic the atom in the crystal).

$^1$H NMR 3a (CDCl$_3$) δ 1.17 (d, 12H, J=6.8 Hz, CH$_3$(iPr)), 1.31 (t, 3H, J=7.3 Hz, CH$_3$ (N-Et)), 2.62-2.75 (m, 2H, CH(iPr)), 3.54-3.63 (m, 2H, CH$_2$(N-Et)), 6.36 (t, 1H, J=6.3 Hz, NH), 7.26 (d, 2H, J=7.7 Hz, m-Ph), 7.44 (t, 1H, J=7.7 Hz, p-Ph).

$^{13}$C NMR 3a (CDCl$_3$) δ 16.57 (CH$_3$(N-Et)) 24.40 (CH$_3$(iPr)), 29.76 (CH(iPr)), 40.39 (CH$_2$(N-Et)), 124.39 (m-Ph), 126.64 (N-Ph), 130.74 (p-Ph), 135.36 (Et-N-isoindole), 147.78 (o-Ph).

$^1$H NMR 3b (CDCl$_3$) δ 1.17 (d, 12H, J=6.8 Hz, CH$_3$(iPr)), 1.34 (t, 3H, J=7.3 Hz, CH$_3$ (N-Et)), 2.64-2.74 (m, 2H, CH(iPr)), 3.58-3.67 (m, 2H, CH$_2$(N-Et)), 4.38 (bs, 1H, NH), 7.26 (d, 2H, J=7.8 Hz, m-Ph), 7.44 (t, 1H, J=7.7 Hz, p-Ph).

$^{13}$C NMR 3b (CDCl$_3$) δ 16.66 (CH$_3$(N-Et)) 24.41 (CH$_3$(iPr)), 29.76 (CH(iPr)), 40.80 (CH$_2$(N-Et)), 124.37 (m-Ph), 125.83 (N-Ph), 130.70 (p-Ph), 147.81 (o-Ph).

EXAMPLE 2

2-(2,6-diisopropylphenyl)-4-(pyridine-3-ylmethyl)-amino)-5,6,7-trifluoroisoindole-1,3-dione (4a) and 2-(2,6-diisopropylphenyl)-5-(pyridine-3-ylmethyl)-amino)-4,6,7-trifluoroisoindole-1,3-dione (4b)

9.5 g (25 mmol) of 2-(2,6-diisopropylphenyl)-4,5,6,7-tetrafluoroisoindole-1,3-dione (2) was dissolved in 15 ml of chloroform (a.r., Molar) and then 1,2-ethylenediamine (2.75 g, 25.5 mmol Aldrich) was added thereto. The solution was stirred for 4 hours and applied to silica gel column, which was equilibrated with chloroform-cyclohexane 1:3 v/v. The column was washed with chloroform-cyclohexane 1:1 v/v, and then eluted with chloroform. The first fractionated product 4a was evaporated (yield: 3.2 g, 26.9%) and the purity of the product was checked by Thin Layer Chromatography (Rf: 0.35 (chloroform)) and the mass of the product was confirmed by Mass Spectrometry (MW+1: 477.5). The second fractionated product 4b was evaporated (yield: 3.1 g, 26.0%) and the purity of the product was checked by Thin Layer Chromatography (Rf: 0.30 (chloroform)) and the mass of the product was confirmed by Mass Spectrometry (MW+1: 477.4).

EXAMPLE 3

2-(2,6-diisopropylphenyl)-4-(2-amino-ethylamino)-5,6,7-trifluoroisoindole-1,3-dione (5a) and 2-(2,6-diisopropylphenyl)-5-(2-amino-ethylamino)-4,6,7-trifluoroisoindole-1,3-dione (5b)

9.5 g (25 mmol) of 2-(2,6-diisopropylphenyl)-4,5,6,7-tetrafluoroisoindole-1,3-dione (2) was dissolved in 15 ml of chloroform (a.r., Molar) and then 1,2-ethylenediamine (1.53 g, 25.5 mmol Aldrich) was added thereto. The solution was stirred for 4 hours and applied to silica gel column, which was equilibrated with chloroform-cyclohexane 1:1 v/v. The column was washed with chloroform-cyclohexane 1:1 v/v, and then eluted with chloroform. The first fractionated product 5a was evaporated (yield: 3.9 g, 37.2%) and the purity of the product was checked by Thin Layer Chromatography (Rf: 0.29 (chloroform)) and the mass of the product was confirmed by Mass Spectrometry (MW+1: 419.6). The second fractionated product 5b was evaporated (yield: 3.9 g, 37.2%) and the purity of the product was checked by Thin Layer Chromatography (Rf: 0.24 (chloroform)) and the mass of the product was confirmed by Mass Spectrometry (MW+1: 419.4).

EXAMPLE 4

2-(2,6-diisopropylphenyl)-4,5,6-trifluoro-7-(2,2,2-trifluoroethylamino)isoindole-1,3-dione (6a) and 2-(2,6-diisopropylphenyl)-4,5,7-trifluoro-6-(2,2,2-trifluoroethylamino)isoindole-1,3-dione (6b)

0.95 g (2.5 mmol) of 2-(2,6-diisopropylphenyl)-4,5,6,7-tetrafluoroisoindole-1,3-dione (2) was dissolved in 15 ml of chloroform (a.r., Molar) and then 2,2,2,-trifluoro-ethylamine (0.23 g, 25.3 mmol Aldrich) was added thereto. The solution was stirred for 4 hours, and then cyclohexane was added (20 ml, Molar) and applied to silica gel column, which was equilibrated with chloroform-cyclohexane 1:3 v/v. The column was washed with chloroform-cyclohexane 1:3 v/v, and then eluted with chloroform-cyclohexane 1:1 v/v. The first fractionated product 6a was evaporated (yield: 510 mg, 43.3%) and the purity of the product was checked by Thin Layer Chromatography (Rf: 0.45 (chloroform-cyclohexane 1:1 v/v)) and the mass of the product was confirmed by Mass Spectrometry (MW+1: 458.2). The second fractionated product 6b was evaporated (yield: 204 mg, 17.3%) and the purity of the product was checked by Thin Layer Chromatography (Rf: 0.25 (chloroform-cyclohexane 1:1 v/v)) and the mass of the product was confirmed by Mass Spectrometry (MW+1: 458.2).

EXAMPLE 5

2-(2,6-diisopropylphenyl)-4-(3-morpholino-4-yl-propylamino)-5,6,7-trifluoroisoindole-1,3-dione (7a) and 2-(2,6-diisopropylphenyl)-5-(3-morpholino-4-yl-propylamino)-4,6,7-trifluoroisoindole-1,3-dione (7b)

9.5 g (25 mmol) of 2-(2,6-diisopropylphenyl)-4,5,6,7-tetrafluoroisoindole-1,3-dione (2) was dissolved in 15 ml of chloroform (a.r., Molar) and then 4-(3-aminopropyl)morpholine (3.67 g, 25.5 mmol Alfa Aesar) was added thereto. The solution was stirred for 12 hours, and applied to silica gel column, which was equilibrated with chloroform-cyclohexane 1:1 v/v. The column was washed with chloroform-cyclohexane 1:1 v/v, and then eluted with chloroform. The first fractionated product 7a was evaporated (yield: 3.7 g, 29.5%) and the purity of the product was checked by Thin Layer Chromatography (Rf: 0.26 (chloroform)) and the mass of the product was confirmed by Mass Spectrometry (MW+1: 503.2). The second fractionated product 7b was evaporated (yield: 3.2 g, 25.5%) and the purity of the product was checked by Thin Layer Chromatography (Rf: 0.23 (chloroform)) and the mass of the product was confirmed by Mass Spectrometry (MW+1: 503.4).

EXAMPLE 6

Detection of Anti-Inflammatory Effect for Inhibition of Preformed TNFα Secretion Matured macrophages produce tumor necrosis factor (TNF-alpha or TNFα) in response to bacterial lipopolysaccharide (*E. coli* LPS, Sigma) stimulation. TNFα production is induced by TNFα bound to the toll-like receptor 4 (TLR-4), the lipopolysaccharide binding protein (LBP), and the CD14 receptor. Secretion of the TNFα is biphasic. For one hour after the stimulation macrophages respond with release of preformed TNFα. Meanwhile, the NF-kappaB signaling pathway turns on the TNFα gene transcription reaching maximum after approximately 8 hours.

In our experiments we investigated the early TNFα secretion of RAW.264.7 matured mice macrophages. This cell line stores large amount of preformed TNFα. The cells were plated into a 24-well plate at a concentration of 600.000 cell/ml 24 hours before the stimulation, and were subsequently stimulated with 100 ng/ml LPS; compounds 3a and 3b of Example 1 were added to part of the samples and a carrier (1% ethylalcohol, which does not effect the TNFα release of the macrophages) were added into the control wells. Culture supernatant was collected and TNFα content was determined by R&D Duoset ELISA kit (detection limit<62.5 pg/ml). Vitality of the cells was monitored by MTS test (3-(4,5-dimethylthiazol-2-yl)-5-(3-carboxymethoxyphenyl)-2-(4-sulfophenyl)-2H-tetrazolium, Promega, Madison, Wis., USA) 3 hours after the stimulation with LPS and no cell death was detected. So the reduced TNFα level was due to inhibition of the release of preformed TNFα and not due to dying of the cells.

Transcription of TNFα gene driven by NF-kappaB activation was measured in RAW.264.7 macrophages transformed by NF-kappaB-luciferase indicator construct after the LPS stimulation. This construct contains a luciferase gene driven by a minimal-promoter. Luciferase activity was measured 6 hours after the LPS stimulation (100 ng/ml), results are presented in FIG. 2b.

Figure 2A:
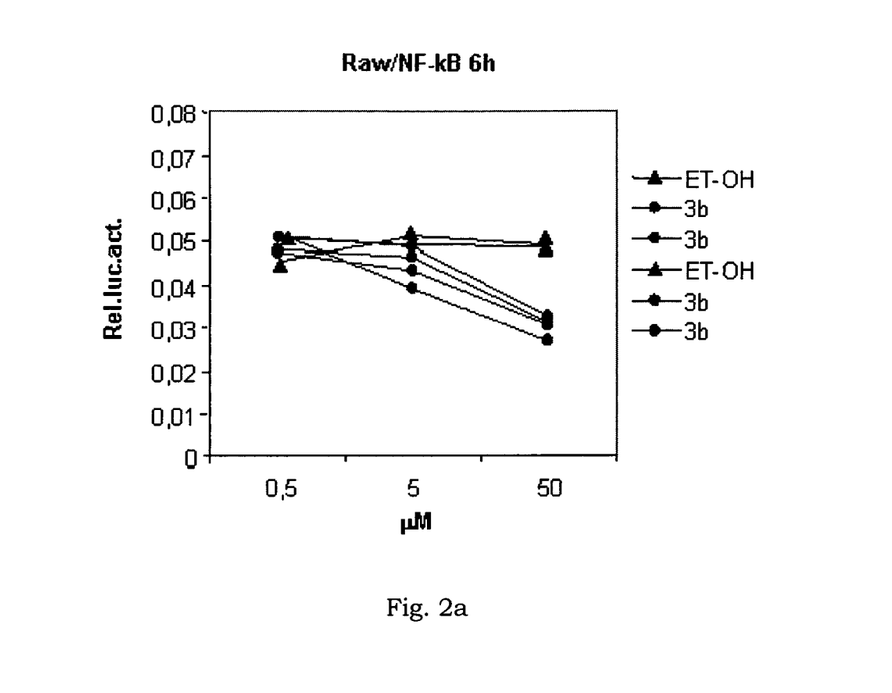
FIG. 2a shows alteration of basal TNFα release of macrophages after treatment with compound 3b.
Figure 2B:
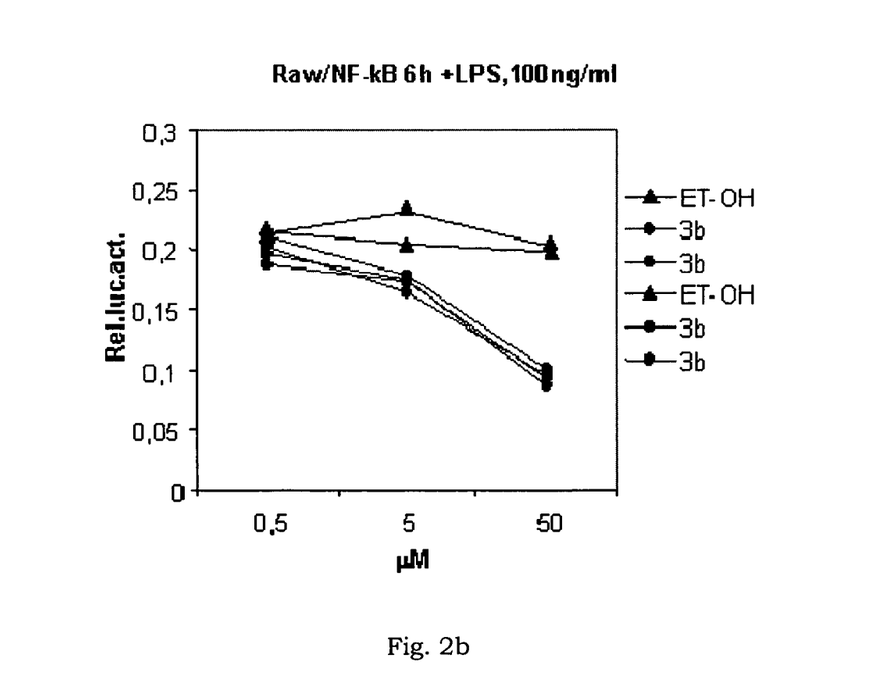
FIG. 2b shows alteration of LPS induced TNFα release of macrophages after treatment with compound 3b.

FIG. 2a shows the alteration of basal TNFα release of the macrophages after treatment with compound 3b., and FIG. 2b shows the effect of compound 3b on LPS stimulated TNFα release of the macrophages. In this example two controls (diluent only—ethanol incubated) and four treated samples were analyzed. It can be seen in FIG. 2a that compound 3b is able to reduce the basal TNFα release of the macrophages even without LPS induction. It can be seen in FIG. 2b that compound 3b reduces the induced TNFα release after LPS stimulation.

EXAMPLE 7

Detection of Anti-Inflammatory Effect for the Inhibition of TNFα Induction

In this example we show the results from experiments with compound 3a and 3b of Example 1.

Figure 3:
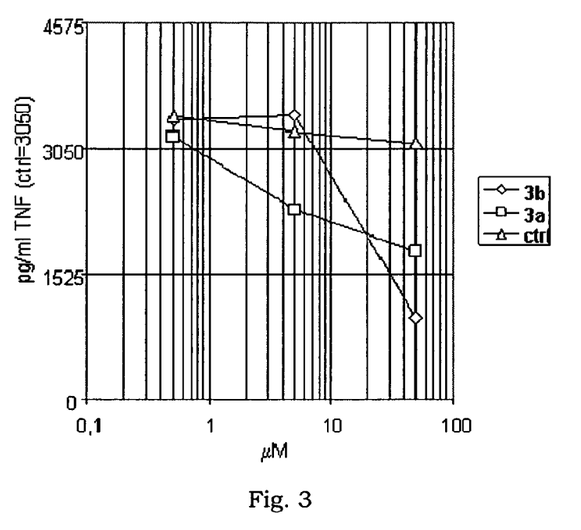
FIG. 3 shows the effect of compounds of the present invention, compound 3a and 3b, on TNFα secretion presented on a logarithmic scale.

For the detection of late phase TNFα secretion the preformed TNFα, released after LPS induction of the macrophages, was washed away after 4 hours, and the amount of TNFα produced during the next 4 hours was determined by ELISA test. In this way we eliminated the TNFα preformed in the macrophages and measured only the amount of transcriptionally induced TNFα that was synthesized and secreted later. Results are depicted in FIG. 3. It can be seen that both compound 3a and compound 3b inhibited late TNFα secretion of macrophages in a concentration dependent way.

Effects of compound 3a and compound 3b on TNFα secretion and on NF-kappaB activation could have been based on cytotoxicity as well. To exclude that, we determined the metabolic activity of the cells, which is proportional to the cell number, by MTS test 8 hours after the treatment. In these assays compounds 3a and 3b were not found to be toxic, i.e. they did not reduce the metabolic activity of the cells.

EXAMPLE 8

Identification of the Interacting Proteins by Affinity Chromatography

By using affinity chromatography we investigated which are the proteins that bind compound 5b of the invention. Compound 5b was linked to cyanobromide activated Sepharose (Amersham-Pharmacia, Sepharose 4B) beads in 6:4 DMF:water mixture for 16 hours at room temperature. 1 ml of the beads was washed with 50 ml 6:4 DMF:water mixture, and then with 50 ml 70% ethanol, then with PBS (0.01 M phosphate buffer, 0.0027 M KCl, 0.137 M NaCl, pH: 7.4). After washing the column 5 ml protein fraction of human MCF-7 breast carcinoma cells (10 million cells homogenized with Complete, Protease Inhibitor Cocktail Tablets, Roche Diagnostics GmbH) were applied onto the column. The column was washed with 20 ml 0.2 M NaCl—PBS solution, then with 15 ml 0.5 M NaCl—PBS solution and with 15 ml 0.8 M NaCl—PBS solution, then it was eluted by 2 ml 2 M NaCl—PBS. The eluate was analyzed by mass spectrometry (LC-MS/MS) to determine the proteins binding to compound 5b.

Mass spectrometry analysis was performed according to the protocol published at http://donatello.ucsf.edu/ingel.html at the time of drafting the patent application.

For the LC-MS/MS analysis 5 µl sample was injected. For the LC precolumn trap was applied: 5 min 20 µl 0.1% trifluoroacetic acid/water, then gradient elution for MS/MS analysis. Columns: Zorbax 300SB-C18, 5 µm, 5×0.3 mm; Zorbax 300SB-C18, 3.5 µm, 150×0.075 mm. Solvents: A1 Solvent: 95.0% (0.1% trifluoroacetic acid/water); B1 Solvent: 5.0% (0.1% trifluoroacetic acid/acetonitrile). MS-method: Scan: m/z 300-1600, MS2 Scan: m/z 100-1800.

With these assays, amongst others, interactions with Rab GTPase proteins were identified. Rab GTPase proteins play a role in intracellular movement of vesicles—including lipid droplets. They were shown to be involved in the development of several diseases including cancer (Kwai W. Cheng et al.: *Emerging Role of RAB GTPases in Cancer and Human Disease. Cancer Res* 2005; 65: (7). Apr. 1, 2005, 2516-2519.).

Our studies revealed that compound 3b can also bind to SEC22b protein being responsible for vesicle movement. This protein can be a candidate target for medicine against the so called legionary disease caused by the microorganism *Legionella pneumophila* (Derre I and Isberg RR: *Legionella pneumophila Replication Vacuole Formation Involves Rapid Recruitment of Proteins of the Early Secretory System*, INFECTION AND IMMUNITY, May 2004, p. 3048-3053).

EXAMPLE 9

Antitumor Activity on Melanoma Cell Line

RVH human melanoma cell line was cultured in Minimum Essential Medium Eagle (Sigma, St. Louis, Mo., USA), Na-piruvate, Glutamine, Non-essential amino acids, penicillin (50 IU/ml)-streptomycin (50 mg/ml), 10% fetal bovine serum at 37° C., in 5% CO2. Cells were trypsinized with trypsin/EDTA (Sigma-Aldrich, St. Louis, Mo.) on every second day and were passed into 60 or 100 mm plates. When the culture reached the required cell number (approx. $10^6$) for the planned experiment 50.00 cell/well was plated into 24 well plates (Costar® 24 Well TC-Treated Microplates) and left overnight to adhere to the bottom of the well. Addition of the substance was performed the following way: next day the culture media was drawn from the adhered cells and media comprising compounds of the present invention in appropriate concentration and well mixed therein was pipetted (2 ml/well) onto the cells. The substance to be examined was diluted in 100% DMSO, this way an amount of DMSO corresponding to the highest concentration of the substance in a given assay were measured in the media of the control wells. After 48 hours of treatment live cells were detected by Cell-Titer® 96 Aqueous Non-radioactive Cell Proliferation Assay (Promega, Madison, Wis., USA) to determine the number of live cells in the treated and in the control samples.

The assay is based on the following:
It contains:
1) MTS: 3-(4,5-dimethylthiazol-2-yl)-5-(3-carboxymethoxyphenyl)-2-(4-sulfophenyl)-2H-tetrazolium) (Promega, Madison, Wis., USA)
2) PMS: phenazine methosulfate (Sigma-Aldrich, St. Louis, Mo.)

MTS is converted to formazane in the living cells, which product is dissolved in the media, and its quantity/absorbance can be measured at 490 nm. Instructions for CellTiter 96® AQueous Assay refers to 96 well plates, and suggest incubating 10.000 cell/well with the different substances under examination. Then, for the determination of the ratio of live cells 20 µl MTS and 1 µl PMS are added to 100 µl media. The enzyme reaction occurs at incubation at 37° C., 5% CO2 for 1 to 4 hours. Formazane produced by the cells is read on ELISA plate reader, from which the number of living cells can be obtained indirectly. Since the inventors performed the experiments in 24 well plates with 50.000 cell/well, the protocol had to be modified. After treatment of the cells for an appropriate time (type of compound, different concentrations), the incubation media (2 ml) containing the examined substance was removed, then 400 µl media containing reagents in the same concentration as given above (333.3 µl media, 66.6 µl MTS, and 3.3 µl PMS per well) was pipetted to the cells. To be able to use ELISA plate reader (Multiskan R C, Thermo Labsystems, Franklin, Mass., USA) 400 µl sample from each single well of the 24 well plate was pipetted into four wells of a 96 well plate (Micromethod plates 96 wells flat form) in 100 µl aliquots. That also helped to eliminate possible errors due to inconsistent pipetting. On each 24 well plate 4 wells were control samples. From these 3 times 100 µl was pipetted onto the 96 well plates, so, altogether 12 controls were provided on each 96 well plate. The remaining 4 wells were for background measurements with 100 µl media containing MTS and PMS as described above.

Figure 4:
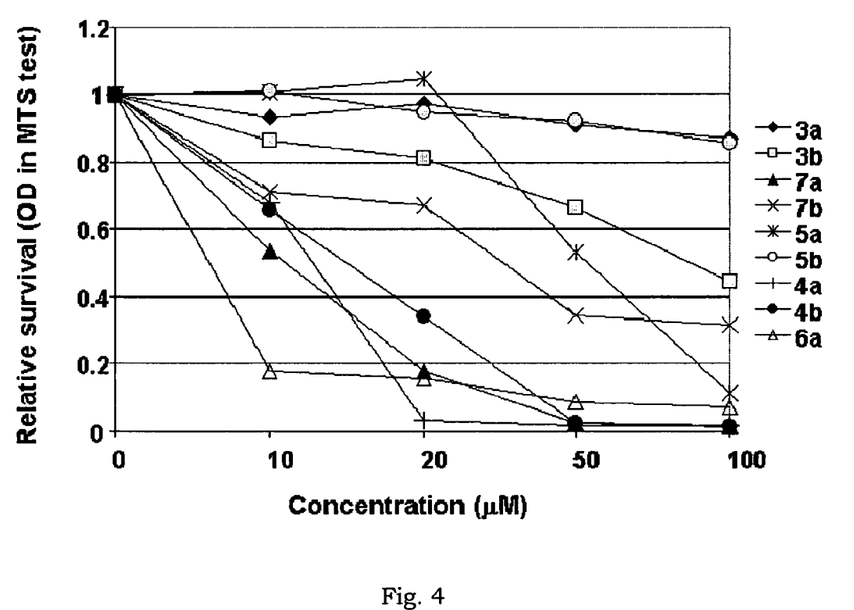
FIG. 4 shows the cytotoxic effect of some compounds of the present invention on RVH human melanoma cell line after 48 hours treatment.

Results are shown in FIG. 4. It can be seen that compounds 3b, 7b, 5a, 4a, 4b, and 6a showed the strongest inhibition. Compounds 5b and 3a exhibited weak effect even at 100 µM concentration on this tumor type.

EXAMPLE 10

Antitumor Activity on Hepatocellular Carcinoma and Breast Carcinoma Cell Lines

In these experiments HepG2 (human Caucasian hepatocellular carcinoma) and MCF7 (Human Caucasian breast adenocarcinoma) cells were used. They were cultured in the following media: For HepG2 Dulbecco's Modified Eagle Medium (D-MEM) (high glucose) (Gibco BRL, Carlsbad, Calif., USA), penicillin (50 IU/ml)-streptomycin (50 mg/ml), 10% fetal bovine serum; for MCF7 (Human Caucasian breast adenocarcinoma) 1:1 mixture of Dulbecco's Modified Eagle Medium (D-MEM) (high glucose) (Gibco BRL, Carlsbad, Calif., USA) and Nutrient Mixture F-12 Ham (Sigma, St. Louis, Mo., USA), penicillin (50 IU/ml)-streptomycin (50 mg/ml), 10% fetal bovine serum. Experiments were performed as described in Example 9. with the difference that the incubation time was 24 hours in this case. After the incubation period MTS test (3-(4,5-dimethylthiazol-2-yl)-5-(3-carboxymethoxyphenyl)-2-(4-sulfophenyl)-2H-tetrazolium) (Promega, Madison, Wis., USA) was performed as described above.

Figure 5:
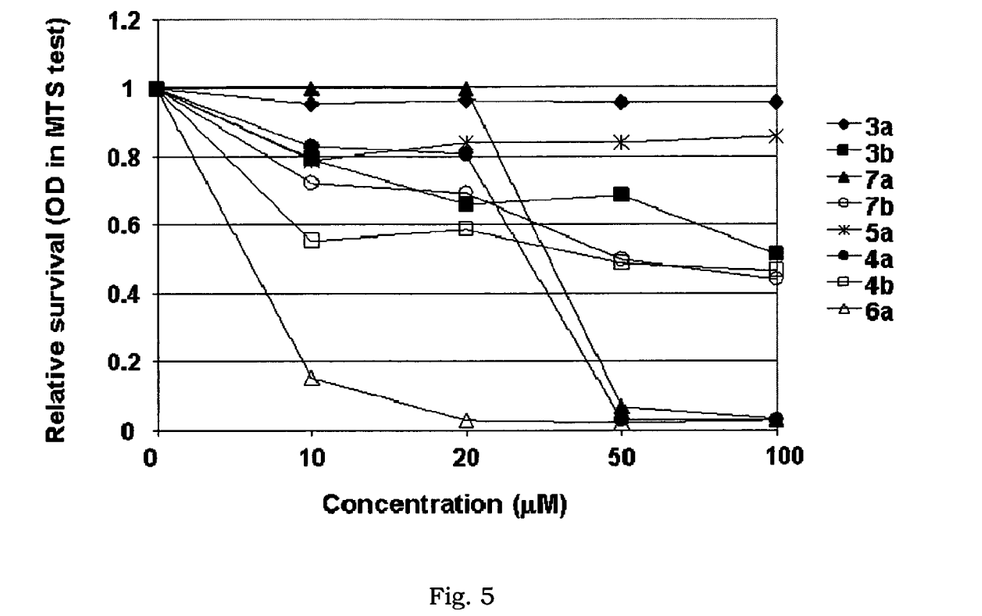
FIG. 5 shows the cytotoxic effect of some compounds of the present invention on MCF7 human breast cancer cell line after 24 hours treatment.

Results from the experiments with HepG2 cells are presented in FIG. 5.

It can be seen that the strongest inhibition was detected with compounds 7a, 7b, 4a and 6a. Compounds 7b, 4b and 3b showed strong effect already at 20 and 50 µM concentrations. Compounds 5a and 3a showed weak effect in the concentration range tested for these tumor types.

Figure 6:
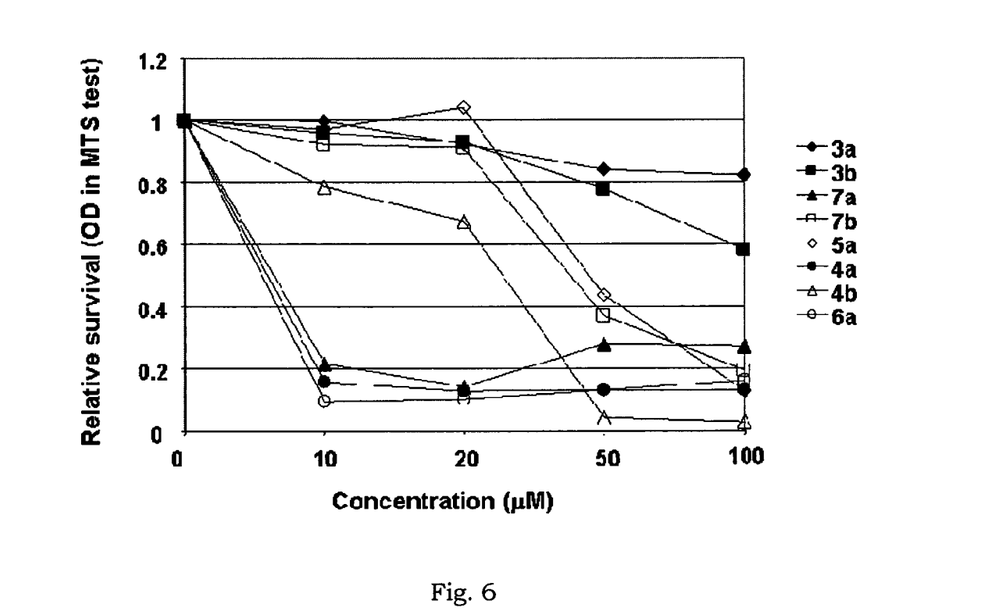
FIG. 6 shows the cytotoxic effect of some compounds of the present invention on HepG2 hepatocellular carcinoma cell line after 24 hours treatment.

Results from the experiments with MCF7 cells are presented in FIG. 6. It can be seen that the strongest inhibition was detected with compounds 7a, 4a and 6a. Compounds 5a, 7b, and 4b showed strong effect already at 20 and 50 µM concentrations. Compounds 3a and 3b showed weak effect in the concentration range tested for these tumor types.

EXAMPLE 11

In Vivo Antitumor Effects I

Figure 7:
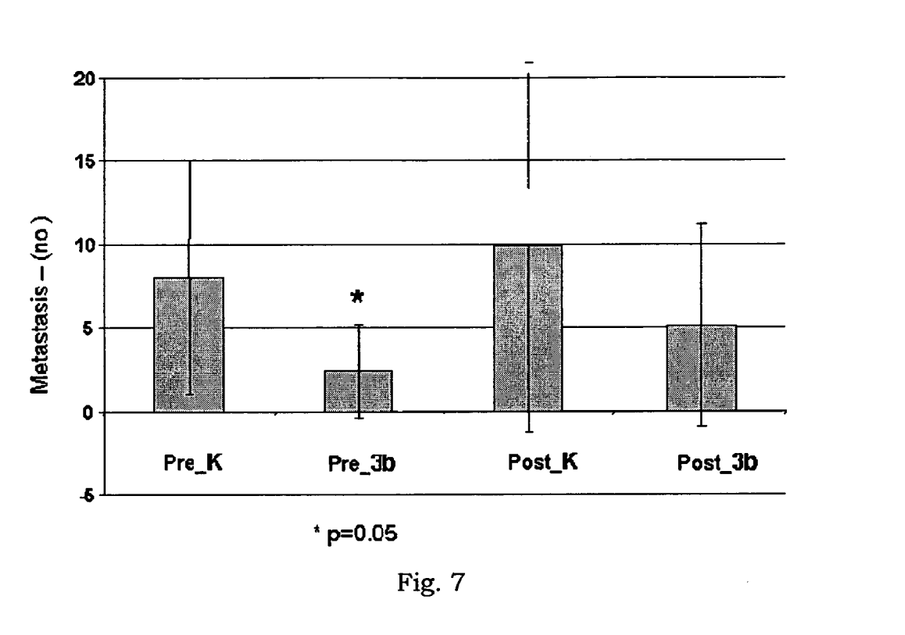
FIG. 7 shows the results of the anti-cancer effect examination in the spleen/liver animal model.

Studies were conducted in the spleen/liver animal model. From 40 adult male CB17/scid mice, born with immunodeficiency, 20 were randomly selected, and they were further divided into two groups. Animals were marked on their ear one by one. 10 of the selected mice were treated with compound 3b (40 mg/kg) for 5 days (PRETREATED/3b), the other 10 animals were treated per os by gavage with appropriate dilution of DMSO serving as the carrier (PRETREATED/control). On the $5^{th}$ treatment day all the 40 animals were anesthetized by Nembutal (75 mg/kg), and $4 \times 10^4$ cells from human melanoma (HT168M1) was injected into their spleens (i.s.). Local bleeding during the implantation was treated with Gelaspon resorbable gelatin sponge. On the $7^{th}$ day after the implantation the non-treated 20 mice were randomly assigned into two groups and their ear was marked. 10 mice were treated from this time on with compound 3b (40 mg/kg) (POSTTREATED/3b), the other 10 were treated with appropriate dilution of the carrier (DMSO) with similar frequency (POSTTREATED/control) per os once a day five times per week for three weeks. Pretreated groups were not treated after the implantation. Body weight changes were monitored once a week for each animal. 31 days after implantation animals were sacrificed by bleeding in Nembutal (75 mg/kg) anesthesia. Evaluation was based on the mass of the primer spleen tumor as well as on the number and size of colonies found in the liver. Results are shown in FIG. 7.

Pretreatment for 5 times significantly reduced the number of metastases ($p=0.05$) when compound 3b was tested. This means that compound 3b inhibits the adhesion of tumor cells, and so, this compound can probably be applied in cases where the primary tumor can be followed by metastasis. This compound inhibits the adhesion of tumor cells present in the circulation, which would otherwise be able to form potential metastases, and so, the chances of survival of the patients can be increased. This effect is so robust that 40 mg/kg dose per os five times was enough to provoke it.

Further metastasis of the adhered cells was also slightly inhibited by the continuous administration of compound 3b in such dose although it did not reach statistical significance, probably due to the large variation of control samples.

EXAMPLE 12

In Vivo Antitumor Effects II

Figure 8:
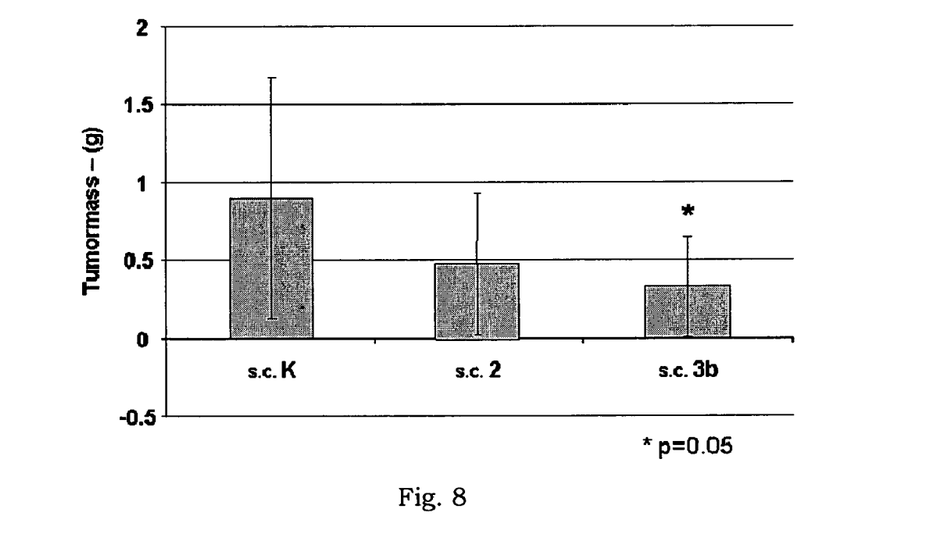
FIG. 8 shows the anti-cancer effects of a compound of the present invention (compound 3b), and a reference compound (compound 2), on a living animal based on tumor mass detection.

Slightly anesthetized (diethyl ether narcosis) adult male CB17/scid mice born with immunodeficiency were subcutaneously (s.c.) implanted with $8 \times 10^5$ cells from in vitro human melanoma (HT168M1) cultures. After tumor cell inoculation animals were randomly assigned into three groups and their ears were marked. From the $7^{th}$ day after the tumor cell inoculation mice were treated once a day five days per week for 3 weeks with compound 2 (40 mg/kg), or with compound 3b (40 mg/kg) per os by gavage. Control animals were treated with appropriate dilution of the carrier (DMSO) in a similar manner with similar frequency. Body weight changes were monitored once a week for each animal. When subcutaneous tumor reached palpable size its dimensions were also detected with caliper. Tumor volume was estimated by the formula $\pi/6 \times a \times b^2$, where "a" is the longer and "b" is the shorter diameter. 30 days after implantation animals were sacrificed by bleeding in Nembutal (75 mg/kg) anesthesia. Evaluation was based on the mass of the primary tumor. Results are shown in FIG. 8.

In this experiment the effect of compound 2 and compound 3b was tested in oral administration at the same dose (40 mg/kg).

It can be clearly seen that the effect of compound 2 on growth of the subcutaneous primary tumor was not significant. In contrast, compound 3b in the same paradigm significantly ($p=0.05$) reduced tumor size. It can be concluded that compound 3b of the present invention was more effective in oral administration for the inhibition of primary tumor growth than compound 2 according to the prior art.

EXAMPLE 13

Demonstration of Antiviral Effect in Cellular Systems

PK-15 porcine kidney cells were infected with approx. 0.001 pfu/cell pseudorabies Bartha type viruses expressing green fluorescent protein (GFP) inserted into Plat2 viral genom. PK-15 cells were investigated at 80% confluency. Cells showing green fluorescence were studied by fluorescent microscopy after 24 hours of incubation at 37° C., 5% $CO^2$. At the time of the infection cells were treated with 100 µM compound 3b (1/100 DMSO 10 mM base solution), and 1/100 DMSO was added to the media as control. The DMSO had no effect on viral plaque formation.

Figure 9:
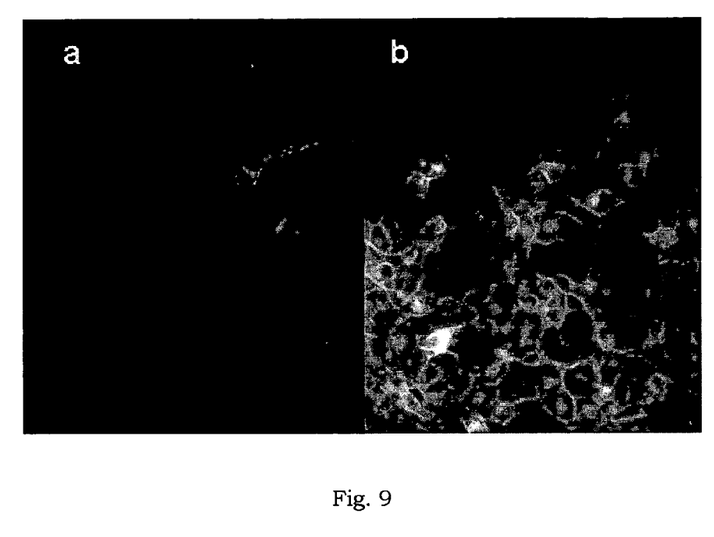
FIG. 9 shows the antiviral effect of a compound of the present invention (compound 3b) against pseudorabies virus.

FIG. 9 shows antiviral effect of 100 µM compound 3b. FIG. 9a presents treated, FIG. 9b presents untreated control cells. It is evident that while in case of untreated control cells green fluorescent viruses formed large plaques (plaque size was several hundred cells), in case of treated cells only a small fraction of the cells (2-6 cells/plaque) showed viral positive signal.

It can be concluded from this experiment that although compound 3b does not inhibit the entry of the viruses into the cell, it does inhibit their release and thus their spreading in vitro.

EXAMPLE 14

Anticancer Effect In Vivo III $2 \times 10^6$ human leukemia cells (K562) from in vitro cultures were injected intravenously (i.v.) into partially narcotized (diethylether narcosis) adult male CB17/scid mice, born with immunodeficiency. After tumor cell inoculation animals were randomly assigned into two groups and their ears were marked. From the 4$^{th}$ day after the tumor cell inoculation mice were treated once a day five days per week for 3 weeks with compound 9a (100 mg/kg), per os (p.o.) by gavage. Control animals were treated with appropriate dilution of the carrier (DMSO) similarly to the treated group with similar frequency. Body weight changes were monitored once a week for each animal according to the ear marks. Evaluation of the effect of the compound was based on the survival of the animals. Results are shown on FIG. 10.

Figure 10:
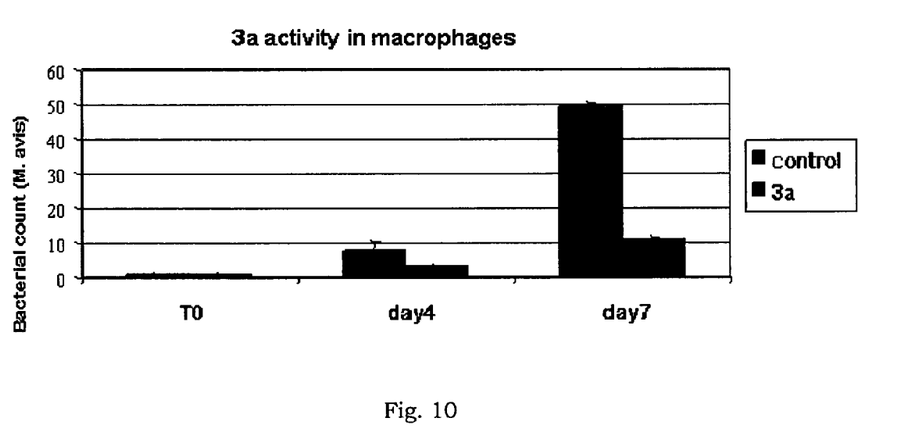
FIG. 10 presents the anti-cancer effect of a compound of the present invention (compound 9a) by showing the survival diagram after cancer cell inoculation.

In this experiment the effects of compound 9a was examined when administered orally using equal concentrations (100 mg/kg). It can be clearly seen that compound 9a resulted in significant increase of the survival of the animals. This result shows that compound 9a of the present invention is effective in the therapeutic use against leukemias.

EXAMPLE 15

Effects Against *Mycobacterium Avis* in Macrophage Culture

Figure 11:
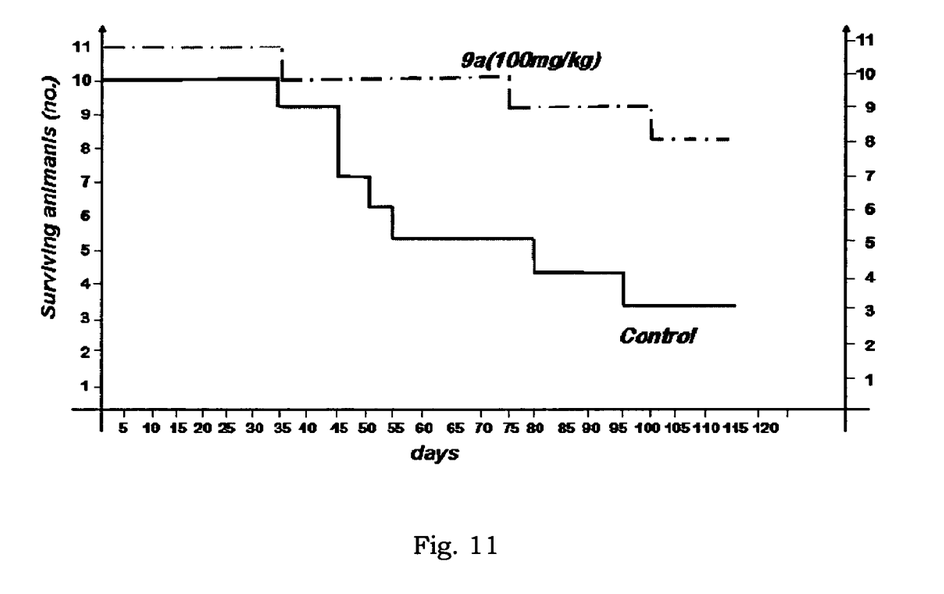
FIG. 11 shows the effects of a compound of the present invention (compound 3a) on *Mycobacterium avis*.

In this experiment the effects of compound 3a were analyzed: the inhibition of *Mycobacterium avis* in macrophage culture was investigated. Human macrophage cells (THP-1) were infected by *Mycobacterium avis* under in vitro conditions, subsequently treated (compound 3a: 36 mg/l) and untreated cells were harvested after different periods of time and the number of the living *Mycobacterium avis* bacteria were determined. Results are shown in FIG. 11. It can be seen that due to compound 3a the number of divided bacteria were significantly smaller than in the untreated group.

From this experiment it is obvious that compound 3a can be effective for the treatment of Mycobacterial infections.

EXAMPLE 16

Synthesis of 2-(2,6-diisopropylphenyl)-4-(3-morpholin)-5,6,7-trifluoroisoindole-1,3-dione (8a) and its effects on different tumor cell lines 8a 9.5 g (25 mmol) of 2-(2,6-diisopropylphenyl)-4,5,6,7-tetrafluoroisoindole-1,3-dione (2) was dissolved in 15 ml of chloroform (a.r., Molar), then morpholine (2.4 g, 27.5 mmol Alfa Aesar) was added. The solution was stirred for 12 hours, and applied to silica gel column, which was equilibrated with chloroform-cyclohexane 1:1 v/v. The column was washed with chloroform-cyclohexane 1:1 v/v, and then eluted with chloroform. The first fractionated product 8a was evaporated (yield: 3.4 g, 29.2%) and its purity was checked by Thin Layer Chromatography (Rf: 0.24 (chloroform)) and the mass of the product was confirmed by Mass Spectrometry (MW+1: 446.1).

The effect of compound 8a was tested on different human and mouse tumor cell lines. We show the results below in Table 1. It can be seen that compound 8a was effective in different leukemias, liver cancer and melanoma.

TABLE 1

| Cell line | 20 µM | 10 µM | 5 µM | 2.5 µM |
| --- | --- | --- | --- | --- |
| HepG2 (liver cancer) | 0.17 | 0.35 | 0.95 | 0.93 |
| HL60 (leukemia) | −0.03 | 0.02 | 0.69 | 0.88 |
| HT168 (melanoma) | 0.06 | 0.06 | 0.44 | 1.07 |
| HT199 (melanoma) | 0.16 | 0.96 | 1.29 | 1.42 |
| K562 (leukemia) | 0.24 | 0.26 | 0.40 | 0.95 |
| MCF7 (breast cancer) | 0.21 | 0.73 | 0.80 | 0.96 |
| P388 (mouse leukemia) | 0.06 | 0.08 | 0.09 | 0.73 |
| WM983 (melanoma) | 0.02 | 0.09 | 0.88 | 0.97 |

EXAMPLE 17

2-(2,6-diisopropylphenyl)-4-(cyclopentylamino)-5,6,7-trifluoroisoindoline-1,3-dione (9a) and 2-(2,6-diisopropylphenyl)-5-(cyclopentylamino-4,6,7-trifluoroisoindoline-1,3-dione (9b)

19 g (50 mmol) of compound 2 (2-(2,6-diizopropylphenyl)-4,5,6,7-tetrafluorisoindolin-1,3-dione) was dissolved in chloroform (30 ml, a.r., Molar), and then cyclopentylamine (8.36 g, 55 mmol), Alfa Aesar) was added. The solution was stirred for 4 hours, then cyclohexane was added (20 ml, Molar) and the solution was applied to silica gel column, which was equilibrated with chloroform-cyclohexane 1:3 v/v. The column was washed with chloroform-cyclohexane 1:3 v/v, then eluted with chloroform-cyclohexane 1:1 v/v. The first fractionated product 9a was evaporated (yield: 6.5 g, 27%) and the purity of the product was checked by Thin Layer Chromatography (Rf: 0.44 (chloroform-cyclohexane 1:1 v/v)) and the mass of the product was confirmed by Mass Spectrometry (MW+1: 445.6). The second fractionated product 9b was evaporated (yield: 5.8 g, 25%) and the purity of the product was checked by Thin Layer Chromatography (Rf: 0.37 (chloroform-cyclohexane 1:1 v/v)) and the mass of the product was confirmed by Mass Spectrometry (MW+1: 445.5).

The invention claimed is:

1. A compound of the general formula I wherein
n is 4;
three of the X substituents are halogen and the fourth X substituent is a heterocyclic or —N—($R^1$, $R^2$) group, wherein each of $R^1$ and $R^2$ independently is hydrogen, an aminoethyl group, or an un-substituted or halogen-substituted group selected from a straight or branched alkyl group, a cycloalkyl group, an aryl group, an aralkyl group, and a heterocyclic group; or $R^1$ and $R^2$ together with the nitrogen in between them form a 5 or 6 member ring;
A is a single bond, —O—, —S— or —NH—;
Y is O or S;
Z is O or S; and
R' and R" are isopropyl groups.

2. The compound according to claim 1, wherein A is a single bond.

3. The compound according to claim 1, wherein at least one of Y and Z is O, or both are O.

4. The compound according to claim 1, wherein $R^1$ is hydrogen.

5. The compound according to claim 1, wherein one or both of $R^1$ and $R^2$ is an un-substituted ethyl group, a halogen substituted ethyl group, or a trifluoro-ethyl group.

6. The compound according to claim 1, wherein one or both of $R^1$ and $R^2$ is an aminoethyl group.

7. A compound selected from the group consisting of:
2-(2,6-diisopropylphenyl)-4-(ethylamino)-5,6,7-trifluoroisoindoline-1,3-dione;
2-(2,6-diisopropylphenyl)-5-(ethylamino)-4,6,7-trifluoroisoindoline-1,3-dione;
2-(2,6-diisopropylphenyl)-4-(2-amino-ethylamino)-5,6,7-trifluoroisoindoline-1,3-dione;
2-(2,6-diisopropylphenyl)-5-(2-amino-ethylamino)-4,6,7-trifluoroisoindoline-1,3-dione;
2-(2,6-diisopropylphenyl)-4,5,6-trifluoro-7-(2,2,2-trifluoroethylamino)isoindoline-1,3-dione;
2-(2,6-diisopropylphenyl)-4,5,7-trifluoro-6-(2,2,2-trifluoroethylamino)isoindoline-1,3-dione;
2-(2,6-diisopropylphenyl)-4-(pyridine-3-ylmethyl)-amino)-5,6,7-trifluoroisoindoline-1,3-dione;
2-(2,6-diisopropylphenyl)-5-(pyridine-3-ylmethyl)-amino)-4,6,7-trifluoroisoindoline-1,3-dione;
2-(2,6-diisopropylphenyl)-4-(3-morpholine-4-yl-propylamino)-5,6,7-trifluoroisoindoline-1,3-dione,
2-(2,6-diisopropylphenyl)-5-(3-morpholine-4-yl-propylamino)-4,6,7-trifluoroisoindoline-1,3-dione;
2-(2,6-diisopropylphenyl)-4-(3-morpholine)-5,6,7-trifluoroisoindoline-1,3-dione;
2-(2,6-diisopropylphenyl)-4-(cyclopentylamino)-5,6,7-trifluoroisoindoline-1,3-dione; and
2-(2,6-diisopropylphenyl)-5-(cyclopentylamino)-4,6,7-trifluoroisoindoline-1,3-dione.

8. A pharmaceutical composition comprising a compound of formula I according to claim 1 and one or more carriers.

9. The composition according to claim 8, wherein A is a single bond.

10. The composition according to claim 8, wherein at least one of Y and Z is O or both are O.

11. The composition according to claim 8, wherein $R^1$ is hydrogen.

12. The composition according to claim 8, wherein one or both of $R^1$ and $R^2$ is an un-substituted ethyl group, a halogen substituted ethyl group, or a trifluoro-ethyl group.

13. The composition according to claim 8, wherein one or both of $R^1$ and $R^2$ is an aminoethyl group.

14. A pharmaceutical composition comprising a compound according to claim 7 and one or more carriers.

15. The compound according to claim 7 that is 2-(2,6-diisopropylphenyl)-4-(3-morpholin-4-yl-propylamino-5,6,7-trifluoroisoindole-1,3-dione.

16. A pharmaceutical composition according to claim 14, wherein the compound is 2-(2,6-diisopropylphenyl)-4-(3-morpholin-4-yl-propylamino-5,6,7-trifluoroisoindole-1,3-dione.

* * * * *